(12) United States Patent
Weisbeck et al.

(10) Patent No.: US 6,753,287 B1
(45) Date of Patent: Jun. 22, 2004

(54) SOL-GEL HYBRID MATERIALS CONTAINING PRECIOUS METALS AS CATALYSTS FOR PARTIAL OXIDATION OF HYDROCARBONS

(75) Inventors: Markus Weisbeck, Köln (DE); Christoph Schild, Leverkusen (DE); Gerhard Wegener, Mettmann (DE); Georg Wiessmeier, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/019,997

(22) PCT Filed: Apr. 11, 2000

(86) PCT No.: PCT/EP00/03214

§ 371 (c)(1),
(2), (4) Date: Oct. 19, 2001

(87) PCT Pub. No.: WO00/64581

PCT Pub. Date: Nov. 2, 2000

(30) Foreign Application Priority Data

Apr. 23, 1999 (DE) .......................................... 199 20 753

(51) Int. Cl.$^7$ .......................... C07D 301/03; B01J 37/00
(52) U.S. Cl. ....................................... 502/107; 549/523
(58) Field of Search ........................... 502/107; 549/523

(56) References Cited

U.S. PATENT DOCUMENTS

| | | | |
|---|---|---|---|
| 3,923,843 A | 12/1975 | Wulff .................... 260/348.5 L |
| 4,410,501 A | 10/1983 | Taramasso et al. .......... 423/326 |
| 4,833,260 A | 5/1989 | Neri et al. ................... 549/531 |
| 5,623,090 A | 4/1997 | Haruta et al. ................ 568/360 |
| 5,929,258 A | 7/1999 | Hayashi et al. | |
| 6,031,116 A | 2/2000 | Bowman et al. ............. 549/523 |
| 6,121,187 A | 9/2000 | Maier | |
| 6,309,998 B1 | 10/2001 | Bowman et al. ............. 502/242 |
| 6,323,351 B1 | 11/2001 | Bowman et al. | |
| 6,524,991 B2 | 2/2003 | Bowman et al. | |
| 2002/0052290 A1 | 5/2002 | Bowman et al. | |
| 2002/0161250 A1 | 10/2002 | Bowman et al. | |

FOREIGN PATENT DOCUMENTS

| | | |
|---|---|---|
| DE | 197 57 496 | 6/1999 |
| DE | 199 18 431 | 10/2000 |
| EP | 0 827 779 | 3/1998 |
| JP | 4-352771 | 12/1992 |
| WO | 98/23023 | 8/1996 |
| WO | 97/47386 | 12/1997 |
| WO | 98/00413 | 1/1998 |

OTHER PUBLICATIONS

Ann. Rev. Mater. Sci. 15, (month unavailable) 1985, pp. 227–248, L.C. Klein, "Sol–Gel. Processing of Silicates".
Adv. Colloid Interface Sci., 5, (month unavailable) 1976, pp. 245–273, S.J. Teichner, G.A. Nicolaon, M.A. Vicarini and G.E.E. Gardes, "Inorganic Oxide Aerogles".
Catal. Rev.–Sci. Eng., 37(4), (month unavailable) 1995, pp. 515–556, Michael Schneider and Alfons Baiker, "Aerogels in Catalysis".

*Primary Examiner*—Taofiq Solola
(74) *Attorney, Agent, or Firm*—Joseph C. Gil; John E. Mrozinski, Jr.

(57) ABSTRACT

The present invention relates to a process for preparing a composition containing gold and/or silver particles and an amorphous, organic/inorganic titanium/silicon mixed oxide, the compositions which can be prepared by this process and their use as catalysts for the selective oxidation of hydrocarbons.

36 Claims, 1 Drawing Sheet

SOL-GEL HYBRID MATERIALS CONTAINING PRECIOUS METALS AS CATALYSTS FOR PARTIAL OXIDATION OF HYDROCARBONS

TECHNICAL FIELD OF THE INVENTION

The present invention provides a process for preparing a composition containing gold and/or silver particles and an amorpous titanium/silicon mixed oxide, compositions which can be prepared in accordance with this process and their use as catalysts for the partial oxidation of hydrocarbons.

BACKGROUND OF THE INVENTION

The sol-gel process is known [L. C. Klein, Ann. Rev. Mar. Sci., 15 (1985) 227; S. J. Teichner, G. A. Nicolaon, M. A. Vicarini and G. E. E. Garses, Adv. Colloid Interface Sci., 5 (1976) 245]. However, this process has not been used hitherto to prepare compositions which contain gold and/or silver particles and an amorphous titanium/silicon mixed oxide, as a method for preparing catalysts for direct oxidation with molecular oxygen as a reducing agent, because the suitability of compositions prepared therefrom for the catalytic oxidation of hydrocarbons has not been disclosed.

SUMMARY OF THE INVENTION

Crystalline titanium silicalite catalysts are known.

U.S. Pat. No. 4,833,260 describes crystalline titanium silicalite catalysts which enable the effective epoxidation of olefins with the oxidising agent hydrogen peroxide in the liquid phase. In silicalites, a small proportion of the silicon in the lattice has been replaced by titanium (U.S. Pat. No. 4,410,501).

On platinum metal-containing titanium silicalites, propene oxidation proceeds with small yields (about 1–2%) and propene oxide selectivities of 60–70% in the liquid phase due to in situ hydrogen peroxide production using a gas mixture consisting of molecular oxygen and molecular hydrogen (JP-A 92/352771, WO 97/47386, WO 96/023 023). Hydrogenations which occur as a secondary reaction lead to large amounts of propane as a secondary product and the fact that this is a liquid phase reaction in which the epoxide being produced accumulates in the liquid phase means that this process is of little interest for industrial use.

U.S. Pat. No. 5 623 090 describes a gas phase direct oxidation of propene to propene oxide with relatively low propene conversions low (0.5–1% propene conversion, with respect to a 10% strength propene feed concentration) but with propene oxide selectivities of >90% with oxygen as the oxidising agent. This is a gold/titanium dioxide catalysed gas phase oxidation with molecular oxygen in the presence of hydrogen at temperatures of 40–70° C. The catalyst which is used is commercially available crystalline titanium dioxide with a very high proportion of the anatase modification (P25, Degussa; 70% anatase and 30% rutile), which is coated with nano-scale gold partides using a deposition-precipitation method. This process has the large disadvantage, in addition to relatively low propene conversions, that the disclosed catalysts deactivate greatly with time. Typical half lives at atmospheric pressure and 50° C. are 30–150 minutes. Increasing the temperature and/or pressure in order to raise the conversion shortens the half lives even further.

In another embodiment, with the same reactant gases, catalysts are used in which gold particles are applied to a support consisting of finely dispersed titanium centres on a silicon dioxide matrix (analogous to the shell variant [U.S. Pat. No. 3,923,843], a heterogeneous titanium and silicon-containing material is used, which is prepared by impregnating $SiO_2$ with titanium precursors in solution) (WO 9800415 A1; WO 9800414 A1; EP 0 827 779 A1). All these catalysts, which are obtained from materials by impregnation of the purely inorganic silica surface with titanium precursors in solution followed by coating with gold by deposition-precipitation and subsequent calcination in an atmosphere of air, exhibit relatively low propene conversion and deactivate rapidly (typical half lives are 10–50 h) and therefore cannot readily be used in industrial scale plant.

WO-98/00413 discloses catalysts in which gold particles are applied to inorganic, microporous, silicates with a crystalline structure with defined pore structures (e.g. TS-1, TS-2, Ti-zeolites such as Ti-beta, Ti-ZSM-48 or titanium-containing, mesoporous molecular sieves such as e.g. Ti-MCM-41 or Ti-HMS). Although all these purely inorganic gold/silicate or gold/zeolite catalysts exhibit good selectivities during partial oxidation, the conversions of hydrocarbons, and in particular the catalyst lifetimes, are inadequate for application in the chemical industry.

The methods described for preparing the catalysts are highly unsatisfactory with respect to catalyst activity and lifetime. Industrial processes which use low activity catalysts require very large reactors. Low catalyst lifetimes restrict production output during the regeneration phases or require duplicated, cost-intensive production routes.

Thus the development of a process to prepare catalysts with which excellent selectivities and high activities can be achieved with industrially relevant lifetimes is required.

Furthermore there is a requirement for a domain-free structure in the catalysts.

There is also the object of reducing the disadvantages in the process according to the prior art.

Another object of the present invention is to provide a technologically simple catalytic gas phase process for the selective oxidation of hydrocarbons with a gaseous oxidising agent on economically viable solid catalysts which leads to high yields and low costs with very high selectivities and industrially relevant catalyst lifetimes.

These objects are achieved according to the invention by the provision of a process for preparing a supported composition which contains gold and/or silver particles and an amorphous titanium/silicon mixed oxide, characterised in that the titanium/silicon mixed oxide is prepared by a sol-gel process and that organic/inorganic sol-gel hybrid systems are preferably prepared.

DETAILED DESCRIPTION OF THE INVENTION

Figure 1:
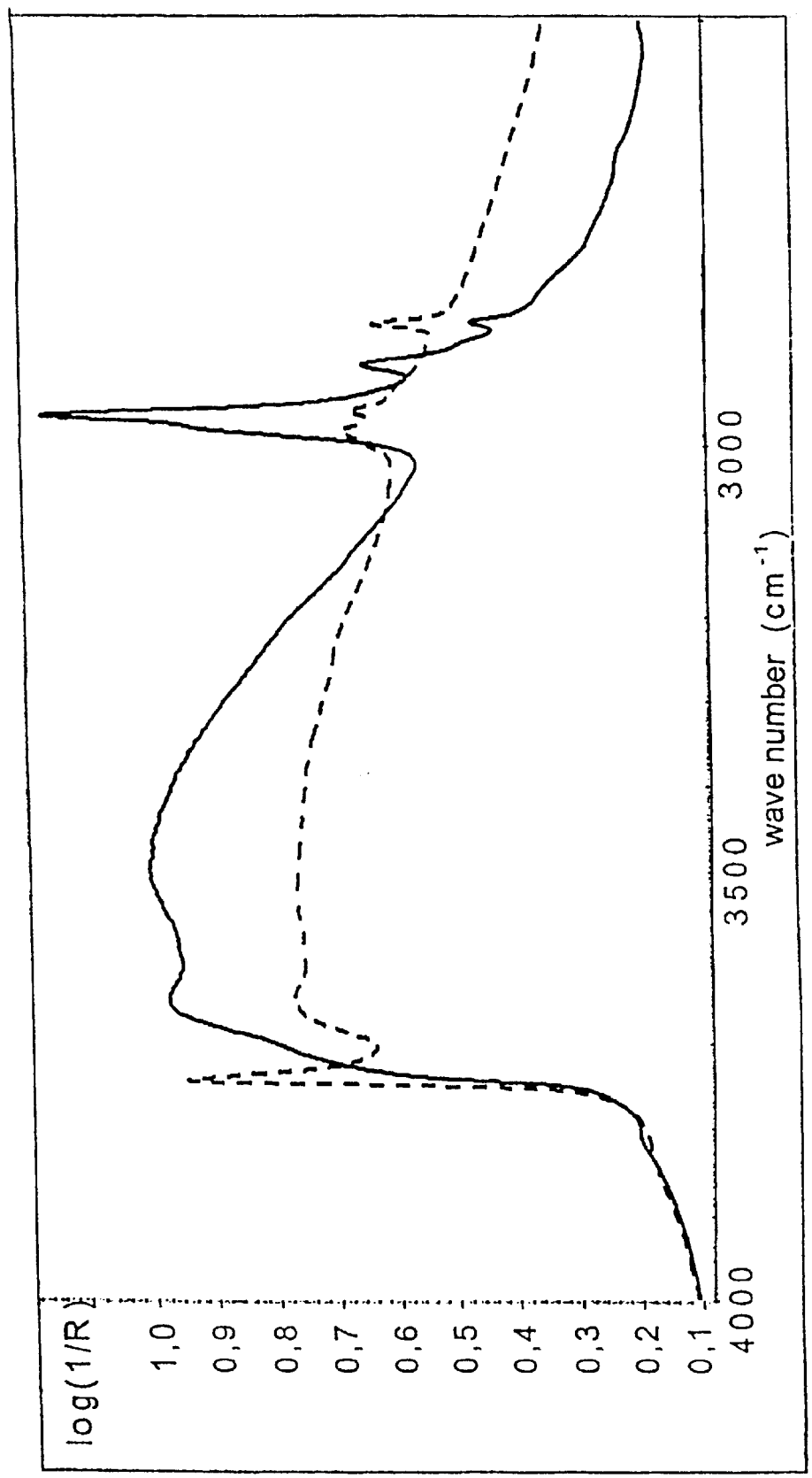
FIG. 1 illustrates the DRIFT spectra of an organic/inorganic hybrid material in accordance with Example 1 and a purely inorganic sol-gel material produced from tetraethoxysilane and tetrabutoxysilane.

The supported composition which can be prepared according to the invention contains gold and/or silver on a support material. In the catalytically-active state, gold and/or silver are mainly present as elemental metals (analysis by X-ray absorption spectroscopy). Small proportions of gold and/or silver may also be present in a higher oxidation state. According to TEM images it has been ascertained that the majority of the gold and/or silver is present on the surface of the support material. These gold and/or silver clusters are present on a nanometre scale. Supported compositions in which the gold particles have a diameter in the range 0.5 nm to 50 nm, preferably 2 to 15 nm and in particular 2.1 to 10 nm are preferred. Silver particles have a diameter in the range 0.5 to 100 nm, preferably 0.5 to 40 nm and in particular 0.5 to 20 nm.

The gold concentration should preferably be in the range 0.001 to 4 wt. %, preferably 0.001 to 2 wt. % and in particular 0.005 to 1.5 wt. % of gold.

The silver concentration should preferably be in the range 0.005 to 20 wt. %, preferably 0.01 to 15 wt. % and in particular 0.1 to 10 wt. % of silver.

Higher gold and/or silver concentrations than the ranges mentioned above do not produce any increase in catalytic activity. For economic reasons the noble metal concentration should be the minimum amount required to provide the highest catalytic activity.

A titanium/silicon mixed oxide in the context of the invention is generally understood to be a silicon component which is chemically combined with a titanium component, e.g. titanium oxide or hydroxide, and optionally other foreign oxides (promoters). This amorphous titanium/silicon mixed oxide is brought into contact with gold and/or silver. The polarity of the surface of a catalyst according to the invention may optionally be adjusted in a targeted manner, e.g. using silylating agents and/or by incorporating hydrophobic groups in the support matrix (e.g. alkyl and/or aryl groups or fluorine).

Production of the noble metal particles on the titanium/silicon-containing mixed oxides is not restricted to one method. To generate gold and/or silver particles, a few examples of methods, such as deposition-precipitation as described in EP-B-0 709 360 on p. 3, line 38 et seq., impregnation in solution, incipient wetness, colloid processes, sputtering, CVD and PVD, are mentioned. It is also possible to integrate precursor compounds of the noble metals directly into the sol-gel process. After drying and annealing the noble metal-containing gels, nano-scale gold and/or silver particles are also obtained. Incipient wetness is understood to be the addition of a solution containing soluble gold and/or silver compounds to support materials, wherein the volume of the solution on the support is smaller than or equal to the pore volume of the support. Thus the support remains dry on a macroscopic scale. Any solvent may be used, as a solvent for incipient wetness, in which the noble metal precursor compounds are soluble, such as water, alcohols, ethers, esters, acetates, ketones, halogenated hydrocarbons, amines, etc.

Nano-scale gold particles produced by the incipient wetness and impregnation methods are preferred. Nano-scale silver particles produced by the incipient wetness, deposition-precipitation and impregnation methods are preferred.

Surprisingly, the generation of nano-scale gold particles from soluble gold compounds, such as tetrachloroauric acid, e.g. by the incipient wetness method, may also take place in the presence of oligomeric or polymeric auxiliary substances such as polyvinylpyrolidone, polyvinyl alcohol, polypropylene glycol, polyacrylic acid, etc. or in the presence of complex-forming components such as cyanides, acetylacetone, ethylacetoacetate, etc. Complex-forming additives such as cyanides, e.g. alkali metal or alkaline earth metal cyanides, are preferably used.

Compositions according to the invention may advantageously be further activated, before and/or after being coated with a noble metal, by thermal treatment at 100–1000° C. in various atmospheres such as air, nitrogen, hydrogen, carbon monoxide, carbon dioxide. Thermal activation at 150–300° C. in oxygen-contaiming gases such as air, or oxygen/hydrogen or oxygen/rare gas mixtures or combinations thereof or under inert gases at 150–1000° C., such as nitrogen and/or hydrogen and/or rare gases or combinations thereof, is preferred. Activation of compositions according to the invention is particularly preferably performed under inert gases in the temperature range 200–600° C. However, it may also be advantageous to anneal the support materials according to the invention at temperatures in the range 200–1000° C. and then to coat these with a noble metal. Thermally activated (annealed) compositions according to the invention frequently exhibit a significantly higher catalytic activity and an extended lifetime when compared with known catalysts.

The mixed oxides in the context of the invention contain between 0.1 and 20 mol % of titanium, preferably between 0.5 and 10 mol %, in particular between 0.6 and 6 mol %, with respect to silicon oxide. The titanium is present in an oxidic form and is preferably chemically incorporated into or bonded to the mixed oxide via Si—O—Ti bonds. Active catalysts of this type contain hardly any Ti—O—Ti domains.

In addition to titanium, compositions according to the invention may contain other foreign oxides, so called promoters, from group 5 of the periodic system according to IUPAC (1985), such as vanadium, niobium and tantalum, preferably tantalum, from group 3, preferably yttrium, from group 4, preferably zirconium, from group 8 preferably Fe, from group 15 preferably antimony, from group 13 preferably aluminium, boron, thallium and metals from group 14, preferably germanium.

For the most part these promoters are advantageously homogeneously distributed, i.e. there is very little domain production. The promoters incorporated, "M", are generally present in the mixed oxide materials in a dispersed form and are advantageously bonded via element—O—Si bonds. The chemical composition of these materials may vary over wide ranges. The proportion of promoter element, with respect to silicon oxide, is in the range 0–10 mol %, preferably 0–4 mol %. Obviously, several different promoters may also be used. The promoters are preferably used in the form of promoter precursor compounds which are soluble in the particular solvent involved, such as promoter salts and/or promoter-organic compounds and/or promoter-organic-inorganic compounds.

These promoters may increase both the catalytic activity of the composition and also the lifetime of the composition in catalytic oxidation reactions of hydrocarbons.

In principle, any crystal structure may be selected for the silicon component, but the amorphous modification is preferred. In principle, any crystal structure may be selected for the titanium oxide, but the amorphous titanium dioxide modification is preferred. The titanium/silicon mixed oxide does not have to be present as a pure component, but may also be present as a complex material, e.g. in combination with other oxides (e.g. titanates). According to our information, the titanium centres which are chemically bonded to silica and/or inorganic silicates, are the catalytically active centres.

The titanium-containing mixed oxide materials are prepared by sol-gel processes. This takes place, for example, by mixing suitable, generally low molecular weight compounds, in a solvent, after which the hydrolysis and condensation reaction is initiated by adding water and optionally catalysts (e.g. acids, bases and/or organometallic compounds and/or electrolytes). Basically, a person skilled in the art knows how to perform such sol-gel processes.

Suitable precursor compounds for silicon, titanium and promoter centres are advantageously corresponding low molecular weight inorganic mixed compounds which are suitable for the sol-gel process or preferably a combination of corresponding inorganic and organic/inorganic mixed compounds. Low molecular weight in the context of the invention means monomers or oligomers. Given sufficient solubility, polymeric precursor compounds of silicon, titanium and promoters are also suitable.

The titanium/silicon mixed oxide is prepared by simultaneous polymerisation of suitable Si and Ti precursors e.g. copolycondensations to give amorphous Xerogels or Aerogels or the like (sol-gel process). This sol-gel process is based on the polycondensation of hydrolysed, colloidally dissolved metal component mixtures (sol) with the production of an amorphous, three-dimensional network (gel). The following schematic diagram is provided as further explanation:

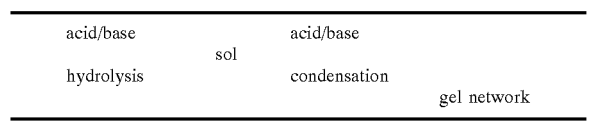

Hydrolysis is performed by initially introducing hydrolysable silicon and titanium precursors into a suitable solvent and then mixing with water and optionally homogenising the mixture with a minimal quantity of dissolution promoter. Since the hydrolysis of silicon precursor compounds under normal conditions is slow, catalysts are required in order to enable it to proceed rapidly and completely (J. Livage et al., Chemistry of Advanced Materials: An Overview (eds: L. V. Interrante et al., VCH, New York, 1998, p. 389–448). The silanols produced condense with the formation of siloxane compounds. Dissolved polysiloxane networks are produced in this way. Branching and transverse cross-linking continues until the polymer is so large that the transition to a gel takes place. The gel initially consists of a solid polymeric network which is infiltrated by solvent. During a subsequent drying procedure, the network shrinks with loss of the solvent, wherein a polysiloxane Xerogel is produced. If the gel is dried under supercritical conditions, the product produced is called an Aerogel (A. Baiker et al., Catal. Rev. Sci. Eng. 1995, 37, 515–556).

Preferred solvents for the sol-gel process are alcohols such as isopropanol, butanol, ethanol, methanol or ketones such as acetone, or ethers or chlorinated hydrocarbons. Suitable starting materials are any soluble silicon and titanium compounds of the general formula (I) known to a person skilled in the art and which may be used as starting materials for the corresponding oxides or hydroxides,

wherein

M' is selected from silicon and titanium,
R and R' are identical or different and are selected, independently, from the group $C_1$–$C_{12}$ alkyl, $C_1$–$C_{12}$ alkylene and $C_6$–$C_{12}$ aryl, wherein x=0, 1, 2, 3 and R' may also be H. Preferably X=1,2 or 3. R' and R can be an alkyl(aryl)silane, e.g. Trimethylsilyl, too.

In the case of preferred organically modified silanes, one or more hydrolysable groups have been replaced by terminal and/or bridged saturated (e.g. $CH_3$, $C_2H_5$, $C_3H_7$, etc.) or by unsaturated (e.g. $C_2H_3$, $C_6H_5$) R group(s). Polyfunctional organo-silanes, e.g. silanols and alkoxides, may also be used. Silanes, whether organically modified or not, are reacted in the presence of dihydric or polyhydric alcohols, such as 1,4-butanediol, to give organically modified polysiloxanes. Bridged R groups (alkylene groups) in the context of the invention are bridged structures such as chain-shaped, star-shaped (branched), cage-shaped or ring-shaped structural elements.

Mixed oxides with organic components are called organic-inorganic hybrid materials. Organic-inorganic hybrid materials according to this invention have terminating or bridging organic groups in the Ti—Si—network. This organic-inorganic hybrid materials are preferred.

Polysiloxanes, e.g. Polydimethylsiloxane (PDMS), optionally with functionalised terminal groups such as hydroxyl or alkoxy, and/or diphenylsilanediol, may also be homogeneously incorporated into the network structure for the purpose of adjusting the polarity of the surface in a targeted manner.

The organic-inorganic silicon- and titanium-precursor compounds can be used in combination with purely inorganic network forming compounds as tertraethoxysilane, tertamethoxysilane, etc. In spite of monomeric alkoxides, the respective condensation products van be used, e.g. $Si(OC_2H_5)_4$. Furthermore oligomeric or polymeric systems, e.g. polydiethoxysiloxanes, can be used.

The modified silanes preferably used here clearly differ from the conventionally used purely inorganic network-producers, such as alkoxysilanes [$Si(OR)_4$] with four hydrolysable groups, which are used e.g. for preparing crystalline silicate structures with defined pore structures (WO-98/00413; TS 1, TS 2, Ti-MCM 41 and 48).

In contrast to catalysts according to the invention, a common feature of all previously known catalysts is that gold particles have been applied to purely inorganic support materials, i.e. that the solid structure consists of purely inorganic silicon/oxygen and titanium/oxygen units.

Alkyl is understood to be any terminal and/or bridged linear or branched alkyl group with 1 to 12 carbon atoms known to a person skilled in the art, such as methyl, ethyl, n-propyl, i-propyl, n-butyl, i-butyl, t-butyl, n-pentyl, i-pentyl, neo-pentyl, hexyl and other homologues which may, for their part, also be substituted. Suitable substituents are halogen, nitro or also alkyl, hydroxide or alkoxy, and cycloalkyl or aryl, such as benzoyl, trimethylphenyl, ethylphenyl, chloromethyl, chloroethyl, and nitromethyl. Non-polar substituents are preferred, such as methyl, ethyl, n-propyl, i-propyl, n-butyl, i-butyl, t-butyl and benzoyl. Higher molecular weight and/or oligomeric organic/inorganic silicon and titanium precursors are also suitable, such as gamma-glycidoxypropyltrimethyloxysilane, 3,4-epoxycyclohexyl-ethyl-trimethoxysilane, 1-(triethoxysilyl)-2-(diethoxymethylsilyl)ethane, tris-(gamma-trimethoxypropyl) isocyanurate, peralkylated cyclosiloxanes such as hexamethylcyclotrisiloxane, octamethyltetrasiloxane or decamethylpentasiloxane. Polyalkyl (aryl)siloxanes such as polydirnethylsiloxane are also suitable.

Aryl is understood to be any mononuclear or polynuclear aryl group with 6 to 12 carbon atoms known to a person skilled in the art, such as phenyl, napthyl or fluorenyl, which, for their part, may also be substituted. Suitable substituents are halogen, nitro or also alkyl or alkoxy, as well as cycloalkyl or aryl substituents, such as bromophenyl, chlorophenyl, toluyl and nitrophenyl. Phenyl, fluorenyl, bromophenyl, chlorophenyl, toluyl and nitrophenyl are preferred.

Examples are the corresponding alkoxides, soluble salts and organosilicon or organotitanium compounds.

Although any salts, such as halides, nitrates and hydroxides may be used, the alkoxides, e.g. butoxide, isopropoxide, propoxide and ethoxide of these elements are preferred.

Titanium derivatives such as tetraalkoxytitanates, with $C_1$–$C_{12}$ alkyl groups, such as iso-butyl, tert-butyl, n-butyl, i-propyl, propyl, ethyl, etc. or other organic titanium species such as titanyl acetylacetonate, dicyclopentadienyltitanium dihalide, titanium dihalogenodialkoxide, and titanium halogenotrialkoxide, preferably in combination with alkyl group containing titanium derivatives, are preferably used. Chlorine is preferred as a halogen substituent. Mixed oxides of titanium and other elements such as e.g. titanium triisopropoxide tri-n-butylstannic oxide may also be used. The titanium precursor compounds may also be used in the presence of complex-forming components such as e.g. acetylacetone or ethylacetoacetate.

The organic/inorganic silicon and titanium precursor compounds may also be used in combination with inorganic network producers such as tetraethoxysilane ($Si(OC_2H_5)_4$) and tetramethoxysilane ($Si(OCH_3)_4$). The condensation products may also be used instead of the monomeric alkoxides. For example, $Si(OC_2H_5)_4$ condensates are commercially available. Furthermore, oligomeric or polymeric systems such as poly(diethoxysiloxane) may also be used.

If small amounts of tetraalkyl orthotitanates are replaced by trialkoxytitanium species, e.g. trialkoxymethyltitanium, the surface polarity may also be adjusted. In addition to monomeric alkoxides, equally effective polymeric systems, such as e.g. poly-(diethoxysiloxanethyl titanate), poly-(octyleneglycol titanate) etc., may be used.

Tetraalkyl orthosilicates such as tetramethyl orthosilicate and/or tetraethyl orthosilicate and trialkoxymethylsilane are preferably used.

Coprecipitates or co-gels of Si, Ti and optionally promoters, Si and Ti, Si and optionally promoters, Ti and optionally promoters, or Si and optionally promoters may also be used as starting compounds in the process according to the invention.

In particular for an industrial scale application, processes based on water glass (an aqueous sodium silicate solution is hydrolysed e.g. after ion-exchange in acids, or a process in which silica is transferred to an organic solvent and then condensed in this medium by acid, neutral or basic catalysts) also provide preferred starting materials in the context of the invention, so that the so-called water glasses are also preferred.

The solvents used in the process according to the invention when using water-sensitive precursor compounds (e.g. alkoxides) are polar organic solvents such as alcohols, e.g. methanol, ethanol, isopropanol, butanol, preferably ethanol, isopropanol or methanol, or other polar organic solvents known to a person skilled in the art which do not have a disadvantageous effect in the sol-gel process such as acetone, sulfolane, or similar solvents, preferably acetone. When using so-called water glasses, water and organic solvents which are miscible with water, such as alcohols, are used, preferably water.

The compositions according to the invention which contain gold and/or silver particles and titanium and silicon-containing materials may be approximately described in the dry state by the empirical general formula (II) given below (groups on the surface formed after modification and optionally incompletely reacted groups are not taken into account here):

$$SiO_x {*} Org {*} TiO_y {*} MO_z {*} E \qquad (II)$$

$SiO_x$ represents silicon oxide, Org represents the organic constituents in the formula, preferably produced in a sol-gel process from the organic/inorganic precursors, M is a promoter, preferably Ta, Fe, Sb, V, Nb, Zr, Al, B, Tl, Y, Ge or combinations thereof, E represents gold and/or silver (noble metal) and x, y and z are the number of oxygen atoms needed for effective saturation of the valences of Si, Ti and M.

The composition called (II) above can be varied over wide ranges.

The proportion of Org as a molar percentage, with respect to silicon oxide, may be between 0 and 300%. It is preferably between 10 and 150%, in particular between 30 and 120%. The proportion of titanium oxide, with respect to silicon oxide is between 0.1 and 10 mol %, preferably between 0.5 and 8.0%, in particular between 2.0 and 7.0%. The proportion of $MO_z$, with respect to silicon oxide, is between 0 and 12 mol %. The proportion of E, with respect to the noble metal-free composition, is between 0.001 and 8 wt. %. In the case of gold it is preferably between 0.001 and 2 wt. %, in the case of silver it is preferably between 0.01 and 15 wt. %.

Furthermore, the objects mentioned above are solved by a process for preparing compositions according to the invention which contain gold and/or silver particles and titanium and silicon-containing materials.

The sequence of operational steps during sol-gel synthesis is not defined. The generation of catalysts according to the invention may be achieved, for example, by simultaneous hydrolysis and/or condensation of Si and Ti precursors, by reaction of organic/inorganic precursor compounds with appropriate Ti compounds followed by the optional addition of the appropriate Si compounds or by simultaneous reaction of organic/inorganic precursor compounds of appropriate titanium and silicon compounds.

In a preferred embodiment, the organic/inorganic silicon precursor compound preferred here is initially introduced into a solvent, hydrolysed, with the addition of a catalyst, using an excess of water, with respect to the amount theoretically required, then the titanium compound is added and further water, optionally along with a catalyst, is added. After the production of a gel, which may take place within from a few minutes to a few days, depending on the composition, the catalyst, the amount of water and the temperature, the gel is dried immediately or after an ageing period of up to 30 days or longer. In order to complete the hydrolysis and condensation reactions, the moist and/or already dried gel may optionally be treated, once or several times, with an excess of water or water vapour. Drying in air or an inert gas is preferably performed at between 50 and 250° C., in particular between 100 and 180° C.

The hydrophobicity of the organic/inorganic hybrid materials according to the invention is determined decisively by the number and type of terminal and bridging Si—C bonds. These have, as compared with other organic bonds such as e.g. Si—O—C bonds, the additional advantage that they are largely chemically inert, i.e. they are insensitive to hydrolysis and oxidation reactions.

The noble metals may be added in the form of precursor compounds, such as salts or organic complexes or compounds, during the sol-gel process, or else applied after production of the gel in a known manner e.g. by precipitation, impregnation in solution, incipient wetness, sputtering, colloids, CVD. Surface modification of the composition is optionally performed after this stage.

Surface modification may be performed either before or after coating with a noble metal. DE 199 18 431.1 describes a supported composition which contains gold and/or silver particles, titanium oxide and a silicon-containing support, which is characterised in that the composition has groups at the surface selected from siliconalkyl, siliconaryl, fluorine-containing alkyl or fluorine-containing aryl groups, and their use as catalysts for the direct oxidation of hydrocarbons. Organic/inorganic hybrid materials have not been disclosed as a support.

Modifications in the context of the invention are understood to be in particular the application of groups selected from siliconalkyl, siliconaryl, fluorine-containing alkyl or fluorine-containing aryl groups to the surface of the supported composition, wherein the groups may be bonded to the functional groups (e.g. OH groups) at the surface in a covalent or coordinate manner. However, any other surface treatment is expressly included within the scope of the invention.

For industrial applications, processes based on waterglass (an aqueous sodium silicate solution is hydrolysed, e.g. after ion-exchange in acids) or processes in which silicic acid is transferred to an organic solvent and is then condensed in this medium under acid, neutral or basic catalysis, also provide suitable titanium/silicon mixed oxides.

In the process according to the invention, acids or bases are used as catalysts for the sol-gel process. Suitable acids and bases are known to a person skilled in the art, from the sol-gel literature such as L. C. Klein, Ann. Rev. Mar. Sci., 15 (1985) 227; S. J. Teichner, G. A. Nicolaon, M. A. Vicarini and G. E. E. Garses, Adv. Colloid Interface Sci., 5 (1976) 245. Inorganic, aqueous or non-aqueous mineral acids such as hydrochloric acid, nitric acid, sulfuric acid, phosphoric acid, hydrofluoric acid or similar and organic acids such as p-toluylsulfonic acids, formic acid, acetic acid, propionic acid, may be mentioned in particular. Hydrochloric acid, nitric acid and p-toluylsulfonic acid are particularly preferred.

The amounts of starting compounds used can be varied over a wide range. Typical molar ratios of hydrolysable Si(Ti) species to water are in the range 0.5–32, preferably 0.5–10.

Suitable catalyst support materials such as e.g. pyrogenic silica, Aerosils and/or Cabosils may also be suspended or dispersed in the colloidal silica sols. Additional condensable, multifunctional molecules such as e.g. monomeric or polymeric glycols, metal halides, cellulose, gelatines or similar compounds may also be used for targeted "material design" purposes; like the hydrolysed alkoxymetallates, these polymers may be incorporated homogeneously into the gel network. The addition of ihydrophobic, organic solvents to the sol phase (dispersed phase), e.g. monofunctional aliphatic alcohols with more than eight carbon atoms, causes the production of an emulsion (dispersed sol phase and homogeneous emulsion liquid) and thus enables design of the material to be customised to a further extent.

The process is performed at pressures in the range from atmospheric pressure to 10 bar, in particular at atmospheric pressure.

The process is performed at temperatures in the range 0–100° C., in particular at 10–60° C.

Any reactors and reactor inserts which have been described in the prior art are suitable as reactors.

The wet gels obtained in the process (called aqua, hydro or alko-gels) are dried in a conventional manner, that is by reducing the pressure and/or by increasing the temperature. The wet gels are advantageously crushed to a powder before drying. If moulded items, not powders, are intended to be formned, the sol is transferred into appropriate shape-providing moulds prior to gelling and then gelled and dried. Conventional drying is often associated with shrinkage of the initially obtained gel structure due to evaporation of liquid from the pores. In order to exchange pore liquid for air while retaining the filigree, solid network (Aerogels), special methods of drying have to be used. "Supercritical drying" with carbon dioxide is the method used most frequently.

Preparation of the final, amorphous, noble metal-containing composition consisting of titanium/silicon mixed oxide and gold and/or silver particles is not restricted in any way.

The noble metal may be added in the form of precursor compounds such as salts or organic complexes or compounds during the sol-gel process, or else may be applied after preparation of the gel in a known manner, e.g. by impregnation, incipient wetness or precipitation. Surface modification of the composition may optionally follow this stage, when the surface OH groups are covered with organic groups. Said surface modification may also take place after preparation of the gel and before application of the noble metal.

Amorphous compositions according to the invention may contain small proportions of crystalline structures.

Although the morphology and particle size of the mixed oxides may be varied over a wide range, homogeneous, amorphous mixed oxides with high surface areas of >20 $m^2/g$, preferably >50 $m^2/g$ are particularly preferred. The specific surface area is determined in a conventional manner using Brunauer, Emmet and Teller's method, J. Anorg. Chem. Soc. 1938, 60, 309, the pore volume is determined by the centrifuge method according to McDaniel, J. Colloid Interface Sci. 1980, 78, 31 and the particle size is determined using Cornillaut's method, Appl. Opt. 1972, 11, 265.

The sol-gel process offers the opportunity of preparing extremely homogeneous and almost completely amorphous titanium/silicon mixed oxides. With high titanium concentrations (>10 wt. %), domain production occurs due to the preferred Ti—O—Ti homocondensation, in which octahedral Ti coordination, known from pure $TiO_2$, prevails. With dilute '$TiO_2$ in $SiO_2$' systems (<10 wt. % of Ti), homogeneous, i.e. domain-free Ti distribution takes place wherein the fourfold coordination preferred by silicon is also taken on by the titanium. These centres are probably the catalytically-active centres (site-isolated centres) used for the selective oxidation of hydro-carbons. In addition the sol-gel process according to the invention is very versatile because gels of almost all metal, semi-metal or non-metallic oxides are known and many of these are suitable for the production of Xerogels and Aerogels, so that the targeted introduction of foreign oxides into the lattice of the titanium/silicon mixed oxides is in principle possible.

We have found that the selectivity and in particular the activity during catalysis of the oxidation of hydrocarbons can be increased if the catalytically active metal centres are incorporated in a defined pore architecture. Secondary reactions can be suppressed in this way. Thus titanium/silicon mixed oxides which have been prepared by a homogeneous copolycondensation process, after coating with a noble metal (gold and/or silver) are highly active, selective, oxidation catalysts. In particular after optional treatment of the surface, these types of systems exhibit excellent selectivities and industrially relevant catalyst lifetimes of weeks and longer.

The optionally present promoters which are described are present for the most part in a homogeneous distribution, i.e. there is very little domain production, thanks to the sol-gel process.

The chemical flexibility of the chemical composition (type of metal, concentration of metal) and targeted modification of the catalyst activity, selectivity and lifetime as a result of optionally performed surface modification, associated with the inhibition of deactivating/blocking processes, characterise the product from the process according to the invention.

Optionally performed surface treatment consists of treating with organic silylating reagents. The resulting compositions are excellent, highly selective redox catalysts.

Suitable silylating reagents are any known silicon compounds which are able to react with the surface OH groups (in a covalent or coordinate manner). For instance, organic silanes, organic silylamines, organic silylamides and their derivatives, organic silazanes, organic siloxanes and other silylating agents and also combinations of silylating reagents may be used as silylating reagents. Partly fluorinated or perfluorinated alkyl(aryl)silicon organic compounds are also understood to be expressly included among silylating compounds.

Specific examples of organic silanes are chlorotrimethylsilane, dichlorodimethyl-silane, chlorobromodimethylsilane, nitrotrimethylsilane, chlorotrimethylsilane, iododimethyl-butylsilane, chlorodimethylphenylsilane, chlorodimethylsilane, dimethyl-n-propyl-chlorosilane, dimethylisopropylchlorosilane, t-butyldimethylchlorosilane, tripropyl-chlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyl-dimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane and 3-cyanopropyldimethylchlorosilane.

Specific examples of organic silylamines are N-trimethylsilylimidazoles, N-t-butyldimethylsilylimidazole, N-dimethylethylsilylimidazole, N-dimethyl-n-propylsilylimidazole, N-dimethylisopropylsilylimidazole, N-trimethylsilyldimethylamine, N-trimethylsilyldiethylaamine, N-trimethylsilylpyrrole, N-trimethylsilylpyrrolidine, N-trimethylsilylpiperidine, pentafluorophenyldimethylsilylamine and 1-cyanoethyl (diethylamino)dimethylsilane.

Specific examples of organic silylamides and their derivatives are N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutyrarnide, N-(t-butyldimethylsilyl)-N-tri-fluoro-acetamide and N,O-bis (diethylhydrosilyl)trifluroacetamide.

Specific examples of organic silazanes are hexamethyldisilazane, heptamethyl-disilazane, 1,1,3,3-tetramethyldisilazane, 1,3-bis(chloromethyl) tetramethyldisilazane, 1,3-divinyl- 1,1,3,3-tetramethyldisilazane and 1,3-diphenyltetramethyldisilazane. Examples of other silylating reagents are N-methoxy-N,O-bistrimethyl-silyltrifluoroacetamide, N-methoxy-N,O-bistrimethylsilyl carbamate, N,O-bistrimethyl-silyl sulfamate, trimethylsilyltrifluoromethane sulfonate and N,N'-bistrimethylsilylurea.

Preferred silylating reagents arc hexamethyldisiloxane, hexamethyldisilazane, chlorotrimcthylsilane, N-methyl-N-trimethylsilyl-2,2,2-trifluoroacetamide (MSTFA) and combinations of these silylating reagents.

Compositions which can be prepared according to the invention may also be subjected to water treatment prior to silylation in order to increase the number of surface silanol groups. Water treatment in this connection means that the catalyst is brought into contact with liquid water or an aqueous saturated ammonium chloride solution and/or ammonium nitrate solution and/or is ion-exchanged with polyvalent cations, e.g. aqueous solutions of $Ca^{2+}$, $Eu^{3+}$ prior to the silylating process step, e.g. the catalyst is suspended in water and then dried (e.g. at 300° C.), or the catalyst is treated with water vapour at >100° C., preferably at 150–450° C., for 1–6 h. The catalyst is particularly preferably treated with water vapour at 200–450° C. for 2–5 h and then dried and surface modified.

Compositions obtainable in the process according to the invention may be used in any physical form at all for oxidation reactions, e.g. powders, milled powders, spherical particles, granules (e.g. produced by spray-drying or spray-granulating), pellets, extnidates, etc.

Compositions obtainable in the process according to the invention are extremely suitable for oxidising hydrocarbons in the gas phase in the presence of gases which contain (atmospheric) oxygen and hydrogen or oxygen and carbon monoxide; this use is another object of the invention.

As a result of gas phase reactions of oxygen and hydrogen in the presence of compositions obtainable by the process according to the invention, epoxides are obtained selectively from olefins, ketones are obtained selectively from saturated secondary hydrocarbons and alcohols are obtained selectively from saturated tertiary hydrocarbons. The catalyst lifetimes, depending on the reactants used, extend to many months or longer.

The relative molar ratio of hydrocarbon, oxygen, hydrogen and optionally a diluent gas may be varied over a wide range.

The molar amount of hydrocarbon used, with respect to the total number of moles of hydrocarbon, oxygen, hydrogen and diluent gas, may be varied over a wide range. An excess of hydrocarbon, with respect to the oxygen used (on a molar basis) is preferably used. The hydrocarbon content is typically greater than 1 mol % and less than 80 mol %. Hydrocarbon contents in the range 5 to 60 mol % are preferred, in particular 10 to 50 mol %.

The oxygen may be used in a wide variety of forms, e.g. molecular oxygen, air and nitrogen oxide. Molecular oxygen is preferred. The molar proportion of oxygen, with respect to the total number of moles of hydrocarbon, oxygen, hydrogen and diluent gas, may be varied over a wide range. The oxygen is preferably used in a molar deficiency with respect to the hydrocarbon. 1–30 mol % of oxygen is preferably used, in particular 5–25 mol % of oxygen.

In the absence of hydrogen, the supported compositions according to the invention exhibit only very low activity and selectivity. Up to 180° C., the productivity in the absence of hydrogen is low, at temperatures above 200° C. large amounts of carbon dioxide are produced in addition to partial oxidation products. Any known source of hydrogen may be used such as e.g. pure hydrogen, synthesis gas or hydrogen from the dehydrogenation of hydrocarbons and alcohols. In another embodiment of the invention, the hydrogen may also be produced in situ in an upstream reactor, e.g. by the dehydrogenation of propane or isobutane or alcohols such as e.g. isobutanol. The hydrogen may also be introduced into the reaction system as a complex-bonded species, e.g. a catalyst/hydrogen complex. The molar proportion of hydrogen, with respect to the total number of moles of hydrocarbon, oxygen, hydrogen and diluent gas, may be varied over a wide range. Typical hydrogen concentrations are greater than 0.1 mol %, preferably 4–80 mol %, in particular 5–65 mol %.

In addition to the reactant gases which are required as essential constituents, a diluent gas, such as nitrogen, helium, argon, methane, carbon dioxide, carbon monoxide or similar gases which behave as fundamentally inert gases, may optionally be used. Mixtures of the inert components described may also be used. The addition of inert components is beneficial with regard to the transport of the heat being released during this exotherinic oxidation reaction and also from a safety point of view.

If the process according to the invention is performed in the gas phase, gaseous diluent components such as, e.g. nitrogen, helium, argon, methane, and optionally water vapour and carbon dioxide may be used. Although water vapour and carbon dioxide are not completely inert, they have a positive effect at very small concentrations (<2 vol. %).

We have found that the selective oxidation reaction described above is very sensitive to the structure of the catalyst. Given the presence of nano-disperse gold and/or silver particles in the supported composition, an advantageous increase in productivity to give the selective oxidation product was observed.

Furthermore, problems related to the diffusion of reactants and products can be minimised when using catalysts according to the invention by deliberately adjusting the polarity of the matrix to the requirements of the catalytic reaction. In order to produce a low polarity for the polymer while retaining sufficient mobility of the reactive centres, cocondensation agents with non-polar hydrocarbons have to be integrated into the polymer. The polarity and swelling behaviour of the support can also be advantageously modified by incorporating oxophilic elements other than silicon, such as boron, aluminium, yttrium, tantalum, zirconium or titanium. The choice of these heteroatoms is restricted, according to the invention, to elements which have redox-stable oxidation states.

Basically, the process according to the invention may be applied to any hydrocarbons. The expression hydrocarbon is understood to mean an unsaturated or saturated hydrocarbon such as olefins or alkanes, which may also contain heteroatoms such as N, O, P, S or halogens. The organic component to be oxidised may be acyclic, monocyclic, bicyclic or polycyclic and may be a monoolefin, diolefin or polyolefin. In the case of organic components with two or more double bonds, the double bonds may be conjugated or non-conjugated. Hydrocarbons are preferably oxidised from which the oxidation products which are produced have partial pressures which are sufficiently low for the product to be continuously removed from the catalyst. Unsaturated and saturated hydrocarbons with 2 to 20, preferably 2 to 10 carbon atoms, in particular ethene, ethane, propene, propane, isobutane, isobutylene, 1-butene, 2-butene, cis-2-butene, trans-2-butene, 1,3-butadiene, pentene, pentane, 1-hexene, 1-hexane, hexadienes, cyclohexene, benzene are preferred.

The invention also provides for use of the compositions which can be obtained in the process according to the invention as catalysts in a liquid phase process for the selective oxidation of hydrocarbons to epoxides in the presence of organic hydroperoxides (R—OOH) or in the presence of gases which contain oxygen and hydrogen or oxygen and carbon monoxide.

Compositions according to the invention can be prepared on an industrial scale in an economically viable process which involves no chemical engineering problems.

The characteristic properties of the present invention arc explained in more detail by the catalyst preparations and catalytic test reactions used in the following examples.

Clearly, it is understood that the invention is not restricted to the following examples.

EXAMPLES

Instructions for testing the catalysts (test instructions)

A metal tubular reactor with an internal diameter of 10 mm and a length of 20 cm and which has been set to a constant temperature by means of an oil thermostat is used. The reactor is supplied with reactant gases using a set of four mass flow regulators (hydrocarbon, oxygen, hydrogen, nitrogen). For reaction, 500 mg of powdered catalyst are initially introduced at 140° C. and at atmospheric pressure. The reactant gases are introduced to the reactor from above. The standard catalyst loading is 3 l/g of catalyst/h. Propene was selected as an example of a 'standard hydrocarbon'. To perform the oxidation reactions, a gas stream enriched with nitrogen was selected, always referred to as a standard gas composition in the following: $N_2/H_2/O_2/C_3H_6 = 14/75/5/6\%$. The reaction gases are analysed quantitatively on a gas chromatograph. Gas chromatographic separation of the individual reaction products is performed by a combined FID/TCD method, in which the gases flow through three capillary columns:

FID: HP innowax, 0.32 mm internal diameter, 60 m long, 0.25 $\mu$m layer thickness:

TCD: the following arc connected in series:
HP-PLOT Q, 0.32 mm internal diameter, 30 m long, 20 $\mu$m layer thickness
HP-PLOT molecular sieve 5 A, 0.32 mm internal diameter, 30 m long, 12 $\mu$m layer thickness:

Example 1

This example describes the preparation of a catalyst consisting of a silicon and titanium-containing, organic/inorganic hybrid material which was coated with gold particles (0.1 wt. %) using incipient wetness. The concentration of non-hydrolysable organic components is 68 mol % and that of titanium is 3.8 mol %, with respect to silicon.

1.9 g of a 0.1 N solution of p-toluenesulfonic acid in water were added to 10.1 g of methyltrimethoxysilane (74.1 mmol) and 15 g of ethanol (AR) and the mixture was stirred for 2 hours. Then 1.46 g of tetrabutoxytitanium (4.3 mmol) were added slowly, the mixture was stirred for a further 30 minutes, 7.1 g of tetraethoxysilane (34.1 mmol) were added, the mixture was stirred for 30 minutes, a mixture of 1.6 g of a 0.1 N solution of p-toluenesulfonic acid in water was added and the mixture was then allowed to stand. The mixture reached gel-point after 3 days. After an ageing period of 48 h, the gel was ground up in a mortar and dried for 8 h at 120° C. under air.

5.4 g of sol-gel material were impregnated with a solution consisting of 540 mg of a 1% strength methanolic gold solution (HAuCl$_4$×3H$_2$O; Merck). which had been made up to 2.8 g with methanol, the macroscopically dry material was dried for 4 h at room temperature and then annealed for 2 h at 400° C. under an atmosphere of nitrogen.

In a test in accordance with the test instructions, a constant PO selectivity of 95% was achieved. The maximum PO yield of 4% was achieved after 2 h, and this dedined to 2.5% after 4 days.

Example 2

This example describes the preparation of a catalyst analogous to example 1, but the gold-containing material dried at room temperature was annealed for 2 h at 400° C. under an atmosphere of hydrogen.

In a test in accordance with the test instructions, a constant PO selectivity of 95% was achieved. The maximum PO yield of 4.1% was achieved after 3 h, and this dedined to 2.8% after 4 days.

Example 3

This example describes the preparation of a catalyst consisting of a silicon and titanium-containing, organic/inorganic hybrid material which was coated with gold partides (0.5 wt. %) by the deposition-precipitation method.

The sol-gel mixture is produced in the same way as in example 1.

2 g of support were initially introduced into 15 ml of methanol (Merck, AR), 20 mg of HAuCl$_4$×3H$_2$O (0.1 mmol, Merck) dissolved in 5 ml of methanol, were added thereto, the pH was adjusted to 8 with 0.5 ml of 1 N Na$_2$CO$_3$ solution, the mixture was stirred for 30 min, 2 ml of monosodium citrate solution (32.1 g/l; pH=8) were added, the pH was checked again and the mixture was stirred for 60 min. The solids were isolated, washed 3 times with 20 ml of methanol each time, dried for 10 h at 120° C. at atmospheric pressure, calcined for 5 h at 200° C. in air and then annealed for 2 h at 400° C. under nitrogen. The gold content of the gold/titanium/silicon catalyst was 0.48 wt. % (ICP analysis).

In a test in accordance with the test instructions, a constant PO selectivity of 95% was achieved. The maximum PO yield of 2.5% was achieved after 1 h, and this declined to 1.5% after 4 days.

Example 4

This example describes the preparation of a purely inorganic catalyst support consisting of the oxides of silicon and titanium, which is coated with gold particles by the precipitation method and then surface-modified.

26 g of tetraethoxysilane (120 mmol, TEOS, Acros, 98%) were added to 22.5 ml of i-propanol, thoroughly mixed and then 2.25 g of 0.1 N HCl were added thereto and the mixture was stirred for 2 h. 1.06 g of tetrabutoxytitanium (3.1 mmol, Acros, 98%) were added dropwise to this solution and the mixture was stirred for 15 min. 23 ml of 2% strength aqueous NH$_3$ solution were added to the homogeneous mixture. The mixture reached gel-point after about 5 min, was allowed to stand for 10 h and then dried, initially for one hour at 120° C. at atmospheric pressure, then for about 20 h under vacuum (50 mbar) and calcined for 3 h at 300° C.

4 g of titanium-containing support were initially introduced into 35 ml of water, 70 mg of HAuCl$_4$ (0.178 mmol, Merck) in 5 ml of water were added thereto, the pH was adjusted to 8 with 1.1 ml of 2 N K$_2$CO$_3$, the mixture was stirred for 30 min and 4 ml of monosodium citrate solution were then added, the pH was checked again and the mixture was stirred for 120 min. The solids were isolated, washed three times with 40 ml of water each time, dried for 10 h at 120° C. at atmospheric pressure and calcined for 3 h at 300° C. The gold content of the gold/titanium/silicone catalyst was 0.52 wt. % (ICP analysis).

2.5 g of substance and 0.5 g of 1,1,1,3,3,3-hexamethyldisilazane (3 mmol, Merck) were initially introduced into dry hexane with stirring, stirred for 2 h at 60° C., the solids were filtered off, washed with 50 ml of hexane and dried for 5 h at 120° C. under vacuum. Surface modification by silylation was then repeated.

In a test in accordance with the test instructions, a constant PO selectivity of 95% was achieved. The maximum PO yield of 1.1% was achieved after 1 h, and this declined to 0.8% after 4 days.

Example 5

This example describes the preparation of a catalyst analogous to example 1, but 60 min after the addition of tetrabutoxytitanium 0.35 g of Ta(OEt)$_5$ (0.75 mmol, Chempur, 99.9%) were added to the homogeneous mixture, stirred for 15 min and the mixture was then gelled, worked up, coated with gold and annealed in the same way as in example 1.

In a test in accordance with the test instructions, a constant PO selectivity of 95% was achieved. The maximum PO yield of 4.6% was achieved after 4 h, and this declined to 4.0% after 4 days.

Example 6

This example describes the preparation of a catalyst analogous to example 1, but 60 min after the addition of tetrabutoxytitanium 220 mg of Al(OC$_4$H$_9$)$_3$ (0.9 mmol, Chempur, 99.9%) were added to the homogeneous mixture, stirred for 15 min and the mixture was then gelled, worked up, coated with gold and annealed in the same way as in example 1.

In a test in accordance with the test instructions, a constant PO selectivity of 95% was achieved. The maximum PO yield of 3% was achieved after 2 h, and this declined to 2.0% after 4 days.

Example 7

Comparison example in accordance with EP-A1-827771

This example describes the preparation of a purely inorganic catalyst support, consisting of the oxides of silicon and titanium, which was coated with gold particles. The silicon and titanium-containing catalyst support was obtained by impregnating silica with titanyl acetylacetonate.

30 g of Aerosil 200 (pyrogeric silicon dioxide, Degussa, 200 m$^2$/g) are suspended in 250 ml of dry methanol, 0.98 g of titanyl acetylacetonate (3.9 mmol, Merck) are added thereto and the mixture is stirred for 2 hr at room temperature. The suspension is evaporated to dryness on a rotary evaporator, the solid is then dried at 130° C. and calcined at 600° C. for 3 hr in a stream of air.

0.16 g of tetrachloroauric acid (0.4 mmol, Merck) is dissolved in 500 ml of distilled water, adjusted to a pH of 8.8 with 2N sodium hydroxide solution, heated to 70° C., 10 g of the titanium-containing silica described above is added thereto and the mixture is stirred for 1 hr. The solid is filtered off, washed with 30 ml of distilled water, dried for 10 hr at 120° C. and calcined for 3 hr at 400° C. in air. The catalyst contains 0.45 wt. % of gold according to ICP analysis.

In a test in accordance with the test instructions, with a PO selectivity of 92%, a propene conversion of 2.3% was achieved after 20 min, the propene conversion was 1.5% after 100 min, the propene conversion was 1.0% after 4 h and the propene conversion was 0.5% after 10 h. Catalyst deactivation increased further with increasing time.

Example 8

Trans-2-butene is selected instead of propene as the unsaturated hydrocarbon. For the partial oxidation of trans-2-butene, an organic/inorganic hybrid catalyst consisting of the oxides of silicon and titanium, and which had been coated with gold particles, is used. The catalyst is prepared in the same way as described in example 1.

In a test in accordance with the test instructions, a constant 2,3-epoxybutane selectivity of 91% was achieved. The maximum yield of 3% was achieved after 2 h, and this declined to 3.0% after 4 days.

Example 9

Cyclohexene is selected instead of propene as the unsaturated hydrocarbon. For the partial oxidation of cyclohexene, an organic/inorganic hybrid catalyst consisting of the oxides of silicon and titanium, which had been coated with gold particles, is used. The catalyst is prepared in the same way as described in example 1. Cyclohexene is taken into the gas phase with the assistance of an evaporator.

In a test in accordance with the test instructions, a constant cyclohexene oxide selectivity of 90% was achieved. The maximum yield of 2.1% was achieved after 3 h, and this declined to 1.8% after 4 days.

Example 10

1,3-butadiene is selected instead of propene as the unsaturated hydrocarbon. For the partial oxidation of 1,3-butadiene, an organic/inorganic hybrid catalyst consisting of the oxides of silicon and titanium, which had been coated with gold particles, is used. The catalyst is prepared in the same way as described in example 1.

In a test in accordance with the test instructions, a constant butene oxide selectivity of 82% was achieved. The maximum yield of 1% was achieved after 4 h, and this declined to 0.7% after 4 days.

Example 11

Propane is used instead of propene, as a saturated hydrocarbon. For the partial oxidation of propane, an organic/inorganic hybrid catalyst consisting of the oxides of silicon and titanium which had been coated with gold particles, is used. The catalyst is prepared in the same way as described in example 1.

In a test in accordance with the test instructions, a constant acetone selectivity of 80% was achieved. The maximum yield of 0.9% was achieved after 4 h, and this declined to 0.7% after 4 days.

Characterising the Catalysts

Organic modification to the external and internal surfaces can be demonstrated, for example, by so-called DRIFTS spectroscopy. DRIFTS (diffuse reflectance infra-red fourier transform spectroscopy) is a well-established vibration spectroscopic method for the structural characterisation of functional groups and adsorbates on solid surfaces. Data on the principle of the method and some application examples from the field of heterogeneous catalysis may be found e.g. in the article by Mestl, G., Knözinger, H., in the Handbook of Heterogeneous Catalysis, Vol. 2, p. 539 et seq. (VCH, Weinheim 1997), and the literature cited therein.

To characterise the catalyst materials according to the invention with and without organic modification to the network, appropriate samples were stored for a few hours at 200° C. in a drying cabinet, transferred to an inert gas cell in the hot state and investigated spectroscopically by means of DRIFTS without further contact with air (to avoid the re-adsorption of $H_2O$ at the surface of the samples).

FIG. 1 shows the DRIFT spectra of an organic/inorganic hybrid material (in accordance with example 1) and a purely inorganic sol-gel material produced from tetraethoxysilane and tetrabutoxysilane). The clearly detectable bands at about 3000 $cm^{-1}$ in the spectrum of the organic/inorganic hybrid material are assigned to the homogeneous incorporation of hydrocarbons ($CH_3$ groups). The purely inorganic material also contains hydrocarbon groups (traces) which possibly arise from the sol-gel process used to prepare the support (these hydrocarbon groups are obviously not fully thermally degraded by treating the material at a temperature of 200° C.).

What is claimed is:

1. A process for preparing a noble metal-containing catalyst comprising:
   (I) preparing a titanium/silicon mixed oxide by a process comprising:
      (a) providing a sol-gel material comprising (i) a titanium component and (ii) a silicon component and, optionally, (iii) an oxide promoter which is not titanium oxide;
      (b) optionally, allowing the sol-gel material to age;
      (c) drying the sol-gel material to form a titanium/silicon mixed oxide; and
   (II) adding gold and/or silver to the titanium/silicon mixed oxide to form a noble metal-containing catalyst.

2. The process according to claim 1, wherein the titanium/silicon mixed oxide is an organic/inorganic hybrid.

3. The process according to claim 1, wherein the titanium/silicon mixed oxide comprises terminal and/or bridging organic groups.

4. The process of claim 1, wherein the drying is performed in air or inert gas at temperatures in the range of between about 50° C. and 250° C.

5. The process according to claim 1, wherein the titanium component is titanium oxide or titanium hydroxide.

6. The process according to claim 1, wherein the optional oxide promoter is vanadium, niobium, tantalum, yttrium, zirconium, antimony, aluminum, boron, thallium or germanium.

7. The process according to claim 1, wherein the titanium component is present is an amount between 0.1 and 20 mol %, based on the amount of the silicon component and, if present, the oxide promoter.

8. The process according to claim 1, wherein the optional oxide promoter is present is an amount in the range from 0 mol % up to about 10 mol %, based on the amount of the silicon component.

9. The process according to claim 1, wherein the titanium component is amorphous.

10. The process according to claim 1, wherein the silicon component is amorphous.

11. The process according to claim 1, wherein the surface of the noble metal-containing catalyst comprises organosilicon and/or fluorine containing organic compounds.

12. The process according to claim 1, wherein the gold and/or silver is present on the surface of the noble metal-containing catalyst in the form of clusters.

13. The process according to claim 1, wherein the gold has a diameter in the range of from about 0.5 to about 50 nm.

14. The process according to claim 1, wherein the silver has a diameter in the range of from about 0.5 to about 100 nm.

15. The process according to claim 1, wherein the concentration of gold added to the titahium/silicon mixed oxide is in the range of from about 0.001 to 4 wt. %, based on the total weight of the noble metal-containing catalyst.

16. The process according to claim 1, wherein the concentration of silver added to the titanium/silicon mixed oxide is in the range of from about 0.005 to 20 wt. %, based on the total weight of the noble metal-containing catalyst.

17. The process according to claim 1, wherein the volume of the gold and/or silver added to the titanium/silicon mixed oxide is equal to or smaller than the pore volume of the titanium/silicon mixed oxide.

18. The process according to claim 1, wherein the surface polarity of the noble metal-containing catalyst is adjustable.

19. The process according to claim 1, wherein the addition of gold and/or silver particles is by deposition-precipitation, impregnation, incipient wetness, colloid processing, sputtering, CVD, PVD or integration.

20. The process according to claim 1, wherein the titanium/silicon mixed oxide is thermally activated.

21. The process according to claim 20, wherein the gold and/or silver is added before or after thermal activation.

22. The process according to claim 20, wherein thermal activation is at temperatures in the range of from about 100° C. to about 1000° C.

23. The process according to claim 20, wherein the thermal activation occurs in air, nitrogen, hydrogen, carbon monoxide, or carbon dioxide at temperatures in the range of from about from about 200° C. to about 800° C.

24. The process according to claim 1, wherein the noble metalcontaining catalyst is thermally activated.

25. The process according to claim 24, wherein thermal activation is at temperatures in the range of from about 100° C. to about 1000° C.

26. The process according to claim 24, wherein thermal activation occurs in air, nitrogen, hydrogen, carbon monoxide, or carbon dioxide at temperatures in the range of from about from about 200° C. to about 800° C.

27. The process according to claim 1, wherein the sol-gel material is formed by:
   a) introducing the silicon component, water and, optionally, a catalyst, into a solvent to form a silicon mixture;
   b) adding the titanium component, water, and, optionally, the oxide promoter, and, optionally a catalyst, into the silicon mixture to form a titanium/silicon mixture;
   c) allowing the titanium/silicon material to gel to form a solgel material.

28. The process according to claim 27, wherein the catalyst is an acid, a base, an organometallic compound and/or an electrolyte.

29. The process according to claim 28, wherein the catalyst is hydrochloric acid, nitric acid, sulfuric acid, phosphoric acid, hydrofluoric acid, p-toluylsulfonic acid, formic acid, acetic acid, or propionic acid.

30. The process according to claim 27, wherein the solvent is methanol, ethanol, isopropanol, butanol, acetone or sulfolane.

31. The process according to claim 27, wherein step a) is a process based on water glass.

32. The process according to claim 31, wherein the solvent in the water glass process is water and an organic solvent which is miscible with water.

33. A process for the oxidation of hydrocarbons in the presence of molecular oxygen and a reducing agent wherein the oxidation of hydrocarbons is conducted in the presence of the noble metal-containing catalyst of claim 1.

34. The process according to claim 33, wherein the hydrocarbon is propene.

35. The process according to claim 34, where propene is oxidized to propene oxide.

36. A noble metal-containing catalyst according to claim 1, wherein the noble metal-containing catalyst is used for the oxidation of hydrocarbons in the presence of molecular oxygen and a reducing agent.

* * * * *